United States Patent [19]

Nicoli et al.

[11] Patent Number: 4,794,806
[45] Date of Patent: Jan. 3, 1989

[54] AUTOMATIC DILUTION SYSTEM

[76] Inventors: David F. Nicoli, 448 Mills Way, Goleta, Calif. 93117; Virgil B. Elings, 1155 Via Tranquilla, Santa Barbara, Calif. 93110

[21] Appl. No.: 14,637

[22] Filed: Feb. 13, 1987

[51] Int. Cl.$^4$ .................. G01N 1/28; G01N 35/00; G01N 1/14; G01N 21/49
[52] U.S. Cl. ................ 73/863.01; 73/864.85; 73/864.87; 250/576; 436/179
[58] Field of Search .......... 73/863.01, 864.85, 864.87, 73/864.21; 436/179; 422/103; 356/36; 250/576

[56] References Cited

U.S. PATENT DOCUMENTS

| | | | |
|---|---|---|---|
| 3,805,831 | 4/1974 | Culbertson | 98/38.5 X |
| 4,036,062 | 7/1977 | Cruzan | 73/863.71 |
| 4,036,063 | 7/1977 | Roof et al. | 73/863.71 |
| 4,070,913 | 1/1978 | Roof | 73/863.71 |
| 4,095,472 | 6/1978 | Mowery, Jr. | 73/864.83 X |
| 4,279,759 | 7/1981 | Pardikes | 210/96.1 X |
| 4,348,112 | 9/1982 | Moreaud et al. | 356/338 |
| 4,408,880 | 10/1983 | Tsuji et al. | 356/338 |
| 4,507,556 | 3/1985 | Brenholdt | 356/338 X |
| 4,633,413 | 12/1986 | Caveney et al. | 73/863.01 X |

Primary Examiner—Tom Noland
Attorney, Agent, or Firm—Charles H. Schwartz; Ellsworth R. Roston

[57] ABSTRACT

A method of and apparatus for an automatic dilution system for providing a variable dilution of an unknown sample material, including a mixing chamber having at least one input and output, sample material and diluent. Injecting a quantity of the sample material into the input of the mixing chamber. Providing a flow of the diluent into the input of the mixing chamber to mix with the sample material and to continuously dilute the concentration of the sample material within the mixing chamber and flowing out of the mixing chamber to provide a variable dilution. Providing a measurement of a particular characteristic of the continuously variable diluted sample material, and controlling the flow of diluent in accordance with an optimal measurement of the particular characteristic.

39 Claims, 2 Drawing Sheets

AUTOMATIC DILUTION SYSTEM

BACKGROUND OF THE INVENTION

1. Field of the Invention

The present invention is directed to an automatic dilution system. Specifically, the present invention provides for an automatic dilution system which ideally provides for an exponential dilution to an appropriate concentration.

2. Description of the Prior Art

The physical or chemical analysis of various types of fluid samples is often accomplished by diluting the sample with a diluent to an appropriate concentration. The fluid samples may be any of a wide variety of solutions, suspensions, and dispersions. As used in the present application, the term "diluent" refers to either a gas or liquid dependent upon whether the dilution application requires the sample to be diluted in a dry or liquid state.

In certain measurement applications, the dilution of the fluid sample is carried out using a known dilution factor. This known dilution factor is either predetermined at the onset of the measurement or is computed after the dilution has been accomplished. In the prior art, a variety of methods and devices have been developed to achieve a known or predetermined dilution of a fluid sample. These prior art methods and devices have been limited in their utility and cannot provide for a variable dilution when such a variable dilution would be more useful than the known or predetermined dilution of the prior art devices.

As an example, the following prior art patents may be pertinent to the present invention. Cruzan U.S. Pat. No. 4,036,062, Roof et al U.S. Pat. No. 4,036,063 and Roof U.S. Pat. No. 4,070,913 all describe means for diluting a liquid sample with liquid diluent in which each of the two fluids is initially contained in a pair of conduits. The two conduits are connected together to permit a closed loop circulation and mixing of the two fluids. The extent of the dilution is determined at the onset by preselecting the volumetric relationship of the two conduits.

The Mowery, Jr. U.S. Pat. No. 4,095,472 describes a system wherein a liquid sample is diluted by directing independent streams of a sample liquid and a liquid diluent each at a constant preset flow rate into a mixing chamber. The diluted sample fluid can then be extracted from the mixing chamber. In this patent a fixed dilution factor is established at the onset. The Culbertson U.S. Pat. No. 3,805,831 describes a mixing apparatus for continuously and proportionally mixing one fluid stream with another. The final sample concentration which emerges is determined by the composition of each stream and their relative rates of flow.

The Pardikes U.S. Pat. No. 4,279,759 describes an optical sensing device to measure the presence of a treatment chemical in a liquid process stream. This patent also controls, by negative feedback, the rate of introduction of the treatment chemical into the continuously flowing stream so as to establish a relatively fixed concentration of the treatment chemical in the stream. Moreaud et al U.S. Pat. No. 4,348,112, Tsuji et al U.S. Pat. No. 4,408,880 and Brenholdt U.S. Pat. No. 4,507,556 describe various sensor techniques based on light scattering and/or defraction to estimate either the particle value or particle concentration in a liquid suspension.

It can be seen, therefore, that a variety of methods and devices exist in the prior art to achieve known or predetermined dilutions of a sample fluid. However, there are other types of measurements of physical or chemical properties of fluid samples wherein the measurement is more properly accomplished by diluting the fluid sample to an extent which is not predetermined at the outset of the dilution process. In these types of measurements, the final extent of dilution may be controlled by some measurable property of the fluid sample which property changes considerably during the dilution process. For example, the measurable property of the fluid sample may be optical turbidity, color, electrical conductivity, pH, etc. The prior art methods and devices cannot provide for this variable dilution which changes during the measurement process in accordance with the change in some measurable property of the fluid sample. The prior art methods and devices are limited in their utility for this type of system.

There are a large number of commercial products which contain fine particles which exist either in a dry state or suspended in an appropriate solvent such as water. The physical and/or chemical properties of these commercial products usually depend significantly on the distribution of particle sizes or molecular weights of the individual particles or molecules contained in the product. Typically, when liquid samples are obtained in a manufacturing process, these samples contain a high concentration of solute particles or macromolecules often exceeding 10% concentration by weight or volume. However, most analytical instruments are designed to measure particle size or molecular weight only if provided with a sample in the form of a dispersion of particles in gas or liquid which is much less concentrated than the concentration normally obtained at the outset from the manufacturing process.

Therefore, there is usually the need to perform a substantial dilution of the original sample. This dilution would normally be accomplished using a fluid diluent which is either a gas or a liquid. For this type of application and for others it would be desirable to develop a simple dilution apparatus which yields an acceptable final dilution of a fluid sample which is appropriate or optimal for the analytical measurement in question. However, the dilution apparatus must ideally operate without any knowledge of the starting concentration or composition of the particular sample, whether in a dry state or in liquid suspension.

In the prior art, dilutions are normally achieved by measuring out a known volume of a starting fluid sample into a suitable container and adding to this, either simultaneously or subsequently, a known volume or amount of diluent. The resulting mixture is then thoroughly mixed so as to disperse the solute particles from the original sample uniformally within the new fluid volume. The result ideally is a new fluid mixture or suspension which is homogeneous and has a lower concentration of the solute component then the original fluid sample at the onset of the dilution process.

As an example, U.S. Pat. Nos. 4,036,062, 4,036,063 and 4,070,913 describe methods of carrying out such a fixed dilution. However, this traditional approach to dilution is inconvenient and relatively inaccurate when large dilution factors are desired. In these situations it is difficult to meter out accurately a very small volume of starting sample fluid to be then added to a given amount of diluent. To overcome this problem it may be necessary to perform multiple dilutions in series in which each individual dilution factor is relatively small and, therefore, accurately controllable. The final dilution factor is then equal to the product of the individual ones. However, such an apparatus is necessarily more complex and more difficult to maintain because of the larger number of individual stages.

In order to perform an analytical measurement a quantity of the new diluted fluid sample is transferred from the mixing container into the appropriate measuring instrument. This transfer is normally provided either by manual means, such as pipetting, or by means of an automatic fluid handling system. Unfortunately, for most analytical instruments the straightforward method of diluting the fluid sample as described above is not very efficient; rather, the dilution factor must often be adjusted in a trial-and-error fashion in order to obtain a final dilution factor which results in optimal performance of the analytical instrument. For example, the initial dilution of the original fluid sample may be insufficient thereby resulting in an overloading or saturation of the measuring instrument. Alternatively, the dilution of the original fluid sample may be too extensive thereby yielding an inaccurate measured signal.

Automatic dilution systems have also been developed which continuously introduce both the starting sample and diluent fluid into the mixing chamber. The input rates of each of these components can be adjusted to fixed known values so as to yield a final diluted fluid sample whose dilution factor remains known. The dilution factor may also be constant in time as some of the final fluid sample is removed from the mixing valume. These systems permit, at least in principle, the dilution factor to be preset to any practical desired value to thereby result in a final solute concentration ranging from a very low value to a very high value of concentration. This type of adjustable dilution system may be seen with reference to U.S. Pat. No. 4,095,472.

Automatic dilution systems have also been developed which rely on the principle of negative feedback. In these systems, one or both of the flow rates of the original sample and diluent into the mixing chamber are continuously adjusted by a mechanism which responds to some measurement of the resulting diluted fluid sample. Typical measurements include turbidity, optical absorbance at a particular wavelength and light scattering intensity, all of which are representative of the solute concentration. The measurement which changes with the concentration of solute particles in the diluent fluid sample is used to automatically adjust the dilutor mechanism so as to yield an approximately unchanging final solute concentration. Such a system is described in U.S. Pat. No. 4,279,759. This type of more sophisticated dilution system is actually an adjustable version of the fixed dilution system described above. However, because of the principle of negative feedback the final solute concentration is kept approximately constant in time with the arrival of addtional sample and diluent. The above described prior art automatic dilution systems provide a background for the automatic dilution system of the present invention which provides for an infinitly variable dilution of a starting fluid sample.

SUMMARY OF THE INVENTION

The present invention is directed to an automatic dilution system and provides for a method and apparatus to obtain a variable dilution of a fluid sample with an appropriate diluent. This type of automatic dilution is useful in applications in which a fixed predetermined dilution factor is not required and, more importantly, is not useful. As an example, one area of analytical measurement in which an automatic dilution system of the present invention is appropriate is particle size analysis.

As an example, in the automatic dilution system of the present invention a measured or unmeasured amount of concentrated original sample is introduced into a mixing chamber. If the original sample is dry material, the concentrated sample can be injected in the form of a quantity of dry powder or a volume of gas in which is suspended dry sample at a high concentration. If the sample is a liquid, then the input sample is a concentrated liquid suspension of solute particles or molecules of the sample. Diluent is then introduced into the same mixing chamber using either the same input as used for the sample, or an additional input. Typically for dry samples the diluent would consist of a pure gas or gas mixture, such as air. For liquid samples, the diluent would be the same liquid solvent used in the original concentrated sample, or perhaps a different liquid.

As fresh diluent is introduced into the mixing chamber, mixed fluid exits the chamber from an output which is preferably located at the furthest point from the input of the starting sample and diluent. The exiting fluid now contains a concentration of sample solute which is lower than the concentration injected into the chamber at the input. This lowering of the concentration is due to the dilution by the diluent flowing within the mixing chamber. The sample solute concentration in the exiting fluid will in general decrease with time as additional fresh diluent is introduced into the chamber. Ideally the exiting concentration of solute decreases or decays exponentially in time provided there is an ideal mixing of the contents of the mixing chamber at all times and the rate of flow of fluid through the chamber is constant.

The peak or maximum solute concentration which initially exits the mixing chamber varies directly with the total amount of sample, S, which is initially injected into the chamber and varies inversely with the volume, V, of the chamber. Incomplete mixing results in a peak concentration value which is either smaller or larger than the ideal value depending upon the fluid flow characteristics within the mixing chamber. The characteristic decay time, $\tau$, of the exponentially decaying solute concentration, $C(t)$, exiting the mixing chamber depends directly on the chamber volume, V, and is inversely proportional to the rate of flow, F, of fresh diluent into the chamber. All of these factors can be combined into a simple mathematical expression for the solute concentration $C(t)$ which exits the mixing chamber as a function of time, t:

$$C(t) = S/V \exp(-t/\tau)$$

where
$$\tau =$$

$$C(t) = S/V \exp(-(F/V)t) \qquad \text{Eq'n 1}$$

The output fluid solute concentration $C(t)$ can, for example, be expressed in units of miligrams per cubic centimeter where the amount of injected solute, S, is given in units of miligrams. The mixing chamber volume, V, is then given in units of cubic centimeters and the rate of flow of fresh diluent, F, is expressed in units of cubic centimeters per second.

The above equation 1 is valid for the idealized case in which the rate of flow, F, of diluent into the mixing chamber is constant in time and the contents of the chamber are thoroughly mixed at every instant of time.

This could also be expressed as the solute concentration being homogeneous throughout the chamber. These conditions can be approximated if the mixing chamber volume, V, is not vastly greater than the volume of sample introduced and/or if the input diluent is injected with sufficient velocity to induce turbulence in the chamber to result in a thorough mixing of the chamber fluid contents by freshly arriving diluent. Alternatively, some mechanical means of stirring the liquid contents of the mixing chamber can be used to insure relative homogeneity throughout the chamber.

Fortunately, the automatic dilution system of the present invention will operate even if the dilution system does not behave in the ideal manner described above. For example, if there is either a non-uniform introduction of diluent or an incomplete or variable mixing of the chamber contents, the output solute concentration, C(t), will not decay in time following a simple exponential law for any interval. C(t) may decay exponentially in time, but the characteristic decay time $\tau$ may vary from one moment to the next depending on the input diluent flow rate and the mixing characteristics of the mixing chamber thereby resulting in an overall nonexponential rate of decay of solute concentration at the output of the mixer.

In general, the solute concentration, C(t), exiting the mixing chamber will decrease with increasing time as the finite amount of sample solute originally introduced into the chamber is flushed from the chamber by the continuous flow of fresh diluent. Whether or not C(t) falls monotonically with time depends on the detailed mixing behavior of the chamber. However, for a properly designed dilutor C(t) will in general decay approximately exponentially with time.

The present invention yields, in principle, an infinitely variable dilution of a starting fluid sample in which the dilution factor of the fluid exiting the dilution device ideally decreases monotonically in time following approximately an exponential decay law. The maximum concentration obtained from this system is achieved at the beginning of the dilution process, essentially at t=0. The more closely matched the mixing volume is to the volume of starting sample initially injected into the chamber, the larger is the initial solute concentration which exits the chamber, C(t=0).

One limit for the system would be where the chamber volume, V, equals the volume of injected sample fluid. With such a chamber volume, the output solute concentration spans the maximum possible range, ranging from the starting injected value to essentially zero after long elapsed times. If on the other hand, the chamber volume, V, substantially exceeds the volume of injected liquid sample, then the peak solute concentration which exits the mixing chamber is substantially smaller than the starting volume. It is, therefore, possible to choose the size of the mixing volume and the volume of initially injected sample to obtain a substantial predilution of an overly concentrated fluid sample, which predilution would occur before the solute concentration is further reduced exponentially in time by the dilutor.

Typically, a fluid sample which is injected into the mixing chamber consists of a relatively small bolus, or pulse, of highly concentrated solute/fluid suspension. As will be described in greater detail, the dilution technique of the present invention can accommodate input sample pulses of almost any volume or starting concentration. For example, injections of the starting samples which are larger in volume and/or higher in solute concentration than normal simply require a longer dilution time to arrive at the same final solute concentration. With the present invention, reproducable sample injections are not a prerequisite for successful use.

In typical applications of the invention, the output from the mixing chamber feeds a length of tubing or pipe which carries the diluted fluid sample to a particular measuring or processing apparatus. Because the exiting solute concentration, C(t), is in general decreasing monotonically and exponentially in time, the solute concentration can be described as a spatially varying function, $C(x,t_0)$, at a particular time ($t_0$) where x refers to linear distance along the tubing which carries the output flow stream measured from the peak in solute concentration in the direction of the static mixer. If the flushing diluent which enters the mixing chamber is introduced at a constant flow rate and if there is complete ideal mixing of the chamber contents at all times, as previously described, then the spatial distribution of solute concentration at a given time ($t_0$), $C(x,t_0)$ is a monotonic decreasing function of distance x. This function is an ideal exponential in distance x provided there is not additional mixing of fluid within the tubing.

If it is desired to obtain a particular dilution of the original fluid sample at some point ($x_0$) or in some small region centered about ($x_0$) along the output flow stream, it is necessary only to stop the flow of flushing diluent into the mixing chamber at the particular instant of time, ($t_0$), at which the solute concentration at ($x_0$) has decayed to the desired value. This solute concentration may be referred to as $C(x_0, t_0)$. At any point ($x_0$), or small region centered about ($x_0$), any desired dilution of the original fluid sample is obtained simply by waiting until the concentration $C(x_0, t)$ falls to the desired value. The only requirement is that a sufficient quantity of original sample, S, be injected into the mixing chamber so as to produce a peak exiting concentration, equal to S/V, which exceeds the desired concentration downstream from the mixing chamber output.

A very useful characteristic of the present invention is its potential for relatively high speed and efficiency in achieving very large dilution factors. Because the solute concentration which exits the mixing chamber, or that at any point $x_0$ along the output flow line decreases exponentially in time, the desired solute dilution at any point ($x_0$) can be achieved relatively quickly even if an excessive amount of sample is originally introduced into the mixing chamber. This desirable property of the present invention will occur provided the system parameters of mixing chamber volume, V, and diluent flow rate, F, are correctly chosen to produce an exponential time constant $\tau$, equal to V/F which is appropriately short, such as on the order of seconds.

For example, a dilutor system may be designed using values for V/F which yield an exponential time constant of, as an example, three seconds. If it is assumed that the sample solute concentration which initially exits the mixing chamber is one hundred times larger than the desired concentration, then after an elapsed time of three seconds after sample injection, the exiting concentration will fall to 1/e or approximately 1/2.7 of the initial exiting value. This is still a factor of 100/2.7, or 37, too large. After two exponential time constants, equal to 6 seconds, the exiting concentration is only 13.5 times too large. Finally, after only 4.6 $\tau$, or approximately 14 seconds, the exiting solute concentration will fall to 1/100 of its original value which is the desired 100:1 additional dilution factor.

It can be seen, therefore, that the powerful nature of the exponential function allows for a much larger initial concentration and still provides for the desired dilution factor within a managable time period. For example, even an initial overconcentration of a factor of 100,000 requires a total elapsed time of only 11.5 decay constants to achieve the desired final concentration. For the above example of $\tau=3$ seconds, this represents only about 35 seconds total time. Therefore, the automatic exponential dilution system of the present invention can achieve fluid sample dilution factors over an enormous dynamic range easily spanning a range of 1,000,000 or greater.

These dilutions are achieved over a relatively short period of time without the need to regulate accurately the flow rate of diluent over this time. In the case of very large dilution factors, it may be useful to use a variable flow rate system. For example, in the initial period following sample injection, it may be appropriate to use a relatively high diluent flow rate, F, which results in a small value for $\tau$ and rapid decay of output solute concentration. When the solute concentration falls to approximately the desired value, the diluent flow rate, F, may be decreased in order to lengthen the time constant $\tau$ and thereby permit more accurate monitoring of the solute concentration so as to be able to halt diluent flow at the proper point in time.

BRIEF DESCRIPTION OF THE DRAWINGS

A clearer understanding of the present invention will be had with reference to the following descriptions and drawings wherein.

DESCRIPTION OF THE PREFERRED EMBODIMENTS

Figure 1:
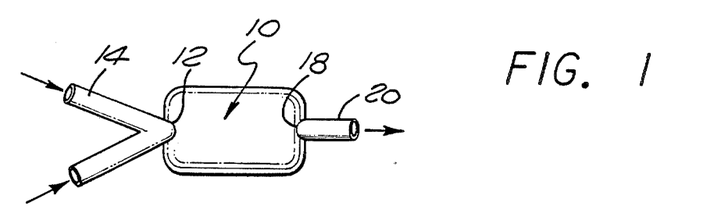
FIG. 1 is a schematic drawing of a simplified embodiment of an exponential dilutor.

FIG. 1 is a schematic drawing of a simplified embodiment showing an exponential dilutor. As shown in FIG. 1 a mixing chamber 10 may be defined to have a volume equal to V. A sample injection may be supplied to the mixing chamber 10 through an input port 12 and with the sample injection provided through input tubing 14. The sample injection may be defined to be an amount equal to S. A flow of diluent is provided through second input tubing 16 which is also connected to the mixing chamber through the input port 12. It is to be appreciated that in place of a single input port 12, separate input ports may be used. The diluent input is provided at a flow rate equal to F.

As fresh diluent continues to be introduced through the tubing 16 into the mixing chamber 10, fluid exits the mixing chamber from an output port 18 preferably located at a point furthest away from the input port 12. The exiting fluid may be passed through output tubing 20 and contains a concentration of sample solute which is lower than the concentration injected into the chamber through the input port 12 because of the mixing with the diluent in the mixing chamber 10. The sample solute concentration in the exiting fluid may be defined as being equal to C(t).

Figure 2:
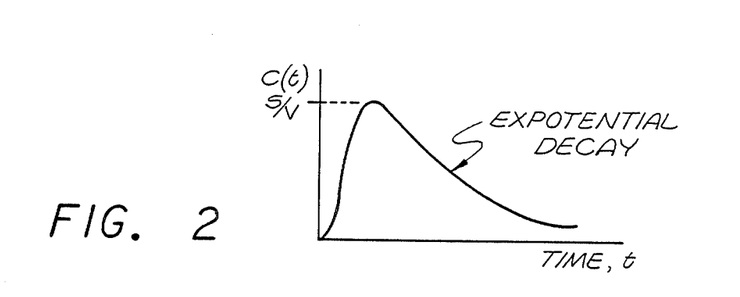
FIG. 2 is a representative plot of output solute concentration exiting the mixing chamber as a function of time.

The exiting solute concentration as a function of time t is shown in FIG. 2. In general, the solute concentration of the exiting fluid decreases with time as additional fresh diluent is introduced into the chamber 10. Ideally, the exiting concentration of solute decreases exponentially in time provided there is ideal mixing of the contents of the mixing chamber at all times and the rate of flow of fluid through the chamber is constant. As shown in FIG. 2, as sample and diluent are introduced into the mixing chamber, the exiting concentration very rapidly builds to a peak and then decays exponentially with time. The peak will vary directly with the total amount of sample S, which is initially injected into the chamber and will vary inversely with the volume of the chamber V. This is shown in FIG. 2.

Before describing specific embodiments of the present invention, it will be useful to consider the application of the exponential dilutor to a particular measurement technology. This technology is particle size determination using the method of Quasi-Elastic Light Scattering (QELS), also known as Photon Correlation Spectroscopy. Diffusion coefficients of particles suspended in liquid solution can be obtained from a mathematical analysis of the autocorrelation function of the intensity of laser light scattered at a particular angle which fluctuates in time due to the Brownian motion of the particles. The particle diameter in turn is obtained from the diffusivity by the Stokes-Einstein law. Typically, colloidal suspensions which are analyzed by the QELS technique are much too concentrated to be measured by a QELS-based instument and therefore require substantial dilution, by a factor from 100 to 1,000,000 in most cases. Dilution of the starting liquid sample is required to reduce the level of light scattering from the suspended solute particles and thereby avoid serious degradation of the performance of the particle sizing instrument due to a variety of physical/optical effects.

Therefore, a dilution system which is appropriate for a QELS-based instrument is one which produces a liquid sample which yields on average a particular level of scattered light from a laser source of fixed intensity. The exponential dilutor system described in the present application is suited to this type of measurement. Specifically, the diluted liquid sample which exits the mixing chamber is directed into a flow-through scattering cell within the instrument. The fluid which exits the instrument cell is discarded or recycled if desired to recover the solute component. The proper dilution factor is obtained by continuously monitoring the light scattering intensity obtained from the measurement cell as the diluted liquid sample flows through the cell. This intensity varies with the solute concentration $C(x_0, t)$ described above, where position variable $x_0$ refers to the measuring point along the output flow stream. When the light scattering intensity falls to the desired level appropriate for an autocorrelation measurement of the particle size, the flow of liquid diluent into the mixing chamber is halted. A particle size measurement may then be accomplished by analyzing the fluctuations in the scattered light intensity which originate from the diluted fluid sample within the same measurement cell. After a measurement has been completed, additional diluent may be flowed through the system to flush out any remaining sample solute from the mixing chamber and output line/scattering cell.

Figure 3:
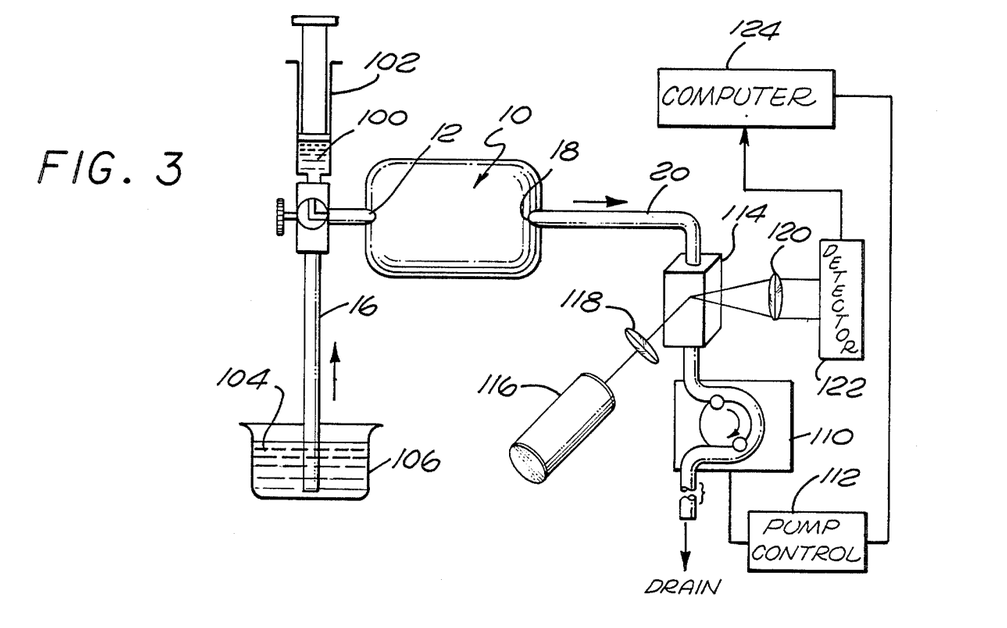
FIG. 3 is a first embodiment of an exponential dilution system applied to a light scattering based instrument.

A specific application of the exponential dilutor system of FIG. 1 to a light scattering based instrument, such as QELS, is shown in FIG. 3. Components of the system of FIG. 3 which are substantially the same as that shown in FIG. 1 are given the same reference characters. Concentrated sample fluid 100 is shown to be contained in a syringe 102. Diluent 104 is shown to be contained in a reservoir tank 106. Both the concentrated sample fluid 100 and the diluent 104 are introduced by the input tubing 14 and 16, respectively, to a three-way valve 108. The output of the three-way valve 108 is directed to the input port 12 of the mixing chamber 10. The three-way valve 108 allows for the introduction of either concentrated sample fluid 100, or diluent 104, but not both at the same time.

Sample injections may be made manually by using the syringe 102, or other means such as a pipetter, through the three-way valve 108. The three-way valve would be in the position shown in FIG. 3 when sample injections are made. It should be appreciated that the injection of the concentrated sample fluid may also be accomplished automatically under computer control using an electrically actuated three-way valve and an external flow pump. After the concentrated sample fluid is introduced into the mixing chamber 10, the three-way valve 108 is reversed in position so as to connect the tubing 16 with the input port 12 of the mixing chamber 10. The diluent fluid 104 may now be introduced into the mixing chamber 10 through the use of a flow pump 110, such as a peristaltic pump. The pump 110 is under control of a pump control 112 but it is to be appreciated that the pump 110 may be manually controlled.

The diluted sample in the mixing chamber 10 exits the chamber 10 through the output port 18 and is passed through the output tubing 20 to a flow through scattering cell 114. The pump 110, therefore, pulls the diluted sample material through the scattering cell 114 and the diluted sample material may then be either discarded, or may be recycled if desired. The scattering cell provides a measurement of the light scattering intensity as a function of time through the use of standard components including a laser source of light 116, a focussing lens 118, an output imaging lens 120 and a detector 122, such as a photomultiplier tube. A representative plot of the light scattering intensity as a function of time obtained from the scattering cell and location $x_0$ is shown in FIG. 4.

Figure 4:
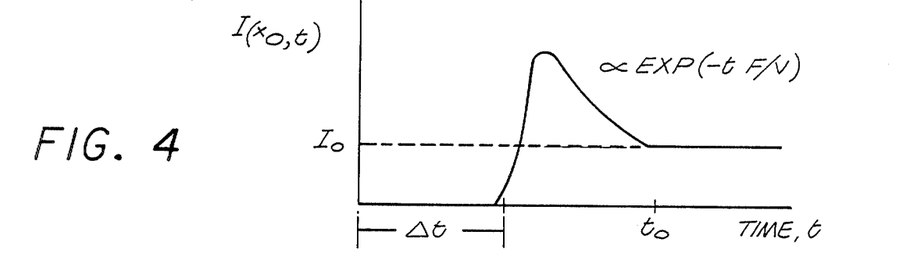
FIG. 4 is a representative plot of the scattering intensity provided by the embodiment of FIG. 3.

As can be seen in FIG. 4, the major features of the plot are an initial steep rise to a peak and a subsequent approximately exponential decay. This curve, shown in FIG. 4, is quite similar to that shown in FIG. 2 with some differences. One difference is that the leading edge of the curve in FIG. 4 is translated in time with respect to that of FIG. 2 by an interval equal to the transit time of liquid from the output port of the mixing chamber 10 at $t=0$ to the measuring cell of the QELS instrument. Another difference in the curve of FIG. 4 is that the light scattering intensity $I(t)$ measured at the scattering cell decays in time only until it reaches the level $I_0$ at which point it remains constant. This level $I_0$ corresponds to a particular solute concentration $C_0$ in the liquid sample. When $I(t)$ falls to this preset level $I_0$ the pump in FIG. 3 is turned off thereby halting the flow of diluent into the mixing chamber 10. This in turn halts the flow of liquid sample through the scattering cell 114. The solute concentration, therefore, remains fixed at level $C_0$ from this point on. A measurement of the solute particle size may then be carried out by the QELS instrument.

The operation of stopping the pump 110 may be accomplished manually by an operator monitoring the light scattering intensity $I(t)$ coming from the flow-through scattering cell 114. Also the pump 110 may be stopped automatically through the use of an output signal from the detector 122 being coupled to a computer 124. The computer may be programmed to control the pump control 112 to turn off the pump 110 at the appropriate time.

The automatic dilution system of the present invention lends itself to simplicity since it requires a minimum of components and moving parts. As shown in FIG. 3, a typical system requires only a mixing chamber, a three-way valve at the input and a pump to pull diluent into the mixing chamber. It is to be appreciated that the pump may be also used to pump diluent into the chamber. The starting sample fluid may be introduced manually or automatically if desired. The system of the present invention may be controlled by an inexperienced operator, since the operator need not be concerned about the amount or concentration of starting sample which is injected into the system. The correct desired final solute concentration, as determined by a measurement of the light scattering intensity, is quickly obtained by the exponential dilution mechanism regardless of the amount and concentration of the starting liquid sample.

In conventional fluid dilution systems, the dilution factor is known because a known amount or rate of flow of concentrated sample is mixed with a known amount or rate of flow of fluid diluent With the present invention, a sample dilution is obtained which is appropriate for the measurement or application in question, but which is usually not known. However, for many applications for which the present invention is useful, this feature of variable unknown dilution is in fact an advantage. The reason for this is that for most unknown samples, it is not known ahead of time what the appropriate dilution factor should be. The scattered intensity for a diluted sample is a function of the initial concentration, the particle size distribution and the index of a fraction of the particles relative to that of the solvent. Therefore, the fact that the dilutor system performs a dilution which at the outset is unknown and which may vary marketly from one sample to the next is not a disadvantage in actual practice. Rather the speed, flexibility and ease of use of the dilutor of the present invention are all distinctive advantages when performing, for example, a particle size measurement on an unknown sample.

In the embodiment of the invention shown in FIG. 3, in general only a small portion of the output from the mixing chamber is used for the particular measurement or application in question. Most of the original concentrated sample which is introduced into the system is not used by the apparatus which receives the diluted sample. This, however, may be in contrast to the situation using conventional systems where it would be desirable to provide for a repeated sampling on a somewhat continuous basis. This may occur when it is desirable to provide for an on-line measurement such as a manufacturing facility.

The automatic dilution system of the present invention may also be applied to the on-line measurement of concentrated fluid mixtures or suspensions. An on-line measurement is typically one which is capable of performing repeated and frequent sampling, dilution and measurement of a fluid sample without operator intervention. Such a capability is useful for monitoring or controlling the physical and/or chemical characteristics of a wide range of materials typically existing in fluid form and produced in a manufacturing facility. Examples of specific characteristics which can be measured include particle size, molecular weight, conductivity, optical absorbance at certain wavelengths, etc.

Figure 5:
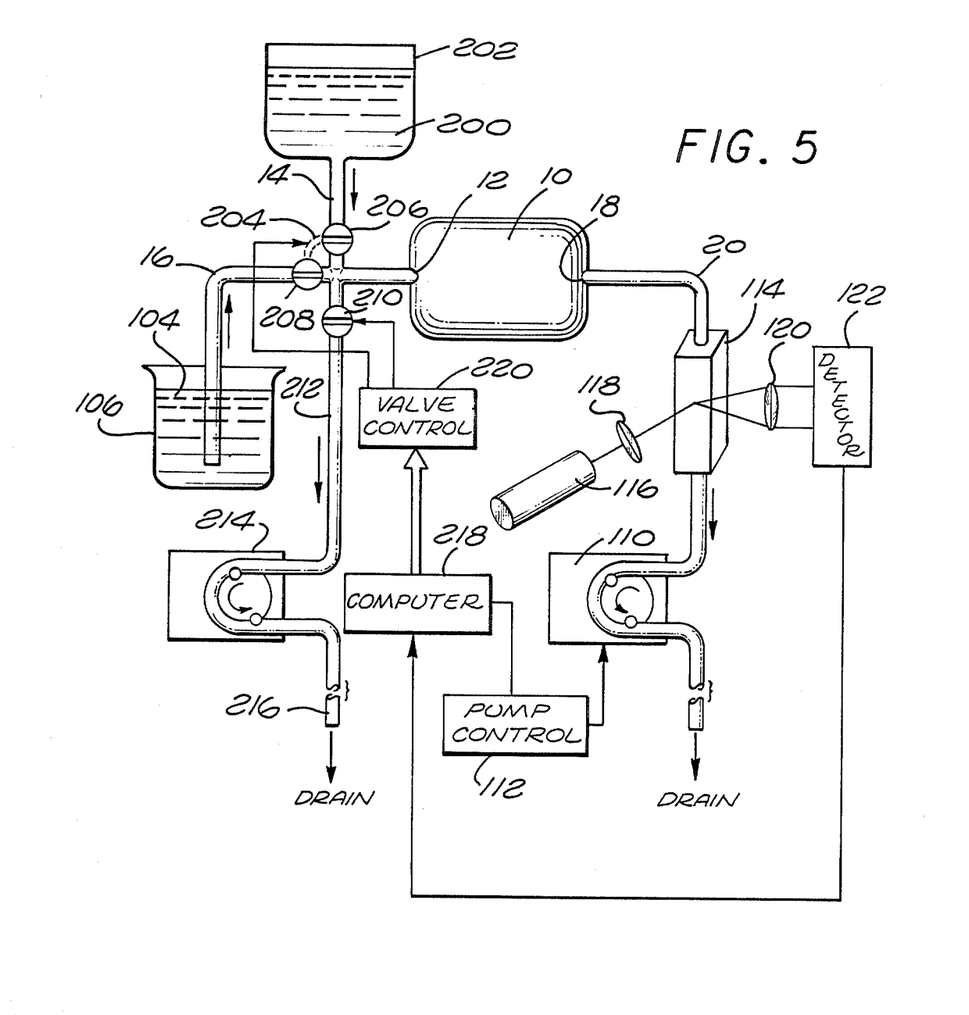
FIG. 5 is a second embodiment of an exponential dilution system appropriate for on-line sample/particle sizing.

FIG. 5 illustrates a particular embodiment of the present invention applied to on-line measurements. In the embodiment of FIG. 5, the measurement of particle size by the dynamic light scattering QELS technique is used. Other elements of the embodiment of FIG. 5 which are substantially the same as those shown in the embodiment of FIG. 3 are given the same reference character. In the embodiment of FIG. 5 the on-line system automatically captures a quantity of concentrated fluid sample from a production process stream or storage tank and continuously dilutes the sample and delivers the diluted fluid sample to a light scattering cell for analysis by a QELS-based instrument. When the scattered light intensity reaches a level appropriate for the measurement, the fluid flow may be halted to stop further dilution and to maintain the sample concentration constant at this level. The system shown in FIG. 5 may either repeat this operation/measurement sequence on a periodic basis or perform a single measurement on demand. Typical particulate systems of commercial interest which may benefit from this on-line particle size monitoring include oil and water emulsions, latex and other synthetic polymer suspensions, ultrafine powder slurries such as ceramics, dyes, pigments, etc., and other colloidal dispersions.

As shown in FIG. 5, the mixing chamber 10 receives through the input port 12 either sample material 200 stored in a storage tank 202 through the input tubing 14 or, diluent 104 in the storage tank 106 through input tubing 16. The flow of either sample material 200 or diluent 104 is controlled by an electrically controlled 3-way valve 204 including, valve portion 206 which is normally closed and valve portion 208 which is normally open. Additionally, a two-way valve 210 which is normally closed is provided in an output tubing 212. Any flow of fluid in the output tubing 212 is provided by a pump 214 (e.g. peristaltic) and out to a drain 216.

The output from the mixing chamber 10 is through the output port 18 and output tubing 20 and into the measurement system including the scattering cell 114. The remaining portion of the measurement system includes the laser 116, the focusing lens 118, the imaging lens 120 and the detector 122. Diluted sample material and diluent are caused to flow through the mixing chamber and the scattering cell 114 by the peristaltic pump 110. The pump 110 is under the control of the pump control 112. The pump control in turn is controlled by a computer 218. The input to the computer is from the detector 122. The computer 218 provides for the control of the pump control 112 and also a valve control 220 in accordance with the output from the detector 122 and additionally any program which forms part of the computer. The valve control 220 individually controls the three-way valve 204 and the two-way valve 210.

It can be seen that the embodiment of FIG. 5 is a modification of the first embodiment of the invention shown in FIG. 3. The modification basically consists of a replacement of the manually operated three-way valve 108 with the electrically operated valve 204. The normally-open portion 208 of the valve 204 is connected to the source of diluent 104 through the tubing 16. The normally-closed portion 206 is connected through the tubing 14 to the source of concentrated sample material 200. As an example, the sample material may be a particle suspension which is to be measured on a frequent basis. This direct connection to the process stream or storage tank 202 replaces the syringe 102 shown in FIG. 3.

In the non-actuated position the three-way valve 204 permits the flow of fluid 104 through the mixing chamber 10 and the light scattering cell 114 caused by the suction of the pump 110 located downstream of the cell 114. If the three-way valve 204 is actuated while the pump 110 continues to run, concentrated sample material 200, rather than diluent 104, now flows into the mixing chamber 10 for as long a period as the three-way valve 204 is energized. When the valve 204 is de-energized, the valve portion 206 and 208 return to their normal positions as shown in FIG. 5 and the flow of concentrated sample 200 into the mixing chamber 10 is halted. Also the flow of fresh diluent 104 recommences thereby initiating the exponential dilution process of the present invention.

There is one potential disadvantage with an on-line sampling apparatus, as shown in FIG. 5, and this is that relatively large quantities of concentrated fluid sample may have to be drawn into the mixing chamber 10, scattering cell 114 and associated tubing when a new measurement is desired. The reason for this is that a "dead" volume exists in the tubing 14 which extends between fresh sample material 200 in the storage tank 202 and the input to the valve portion 206 of three-way valve 204. The further the sample source 200 in the storage tank 202 is from the three-way valve 204, the larger is the dead volume. In order to perform a measurement on a fresh fluid sample, the old stagnant sample contained in this dead volume must be completely displaced by new sample fluid. If the dead volume is not displaced, the measurement will reflect the property of the old sample captured from the source of sample material 200 at the time of the previous measurement.

One method of overcoming this problem is simply to inject a relatively large quantity of concentrated fluid sample into the mixing chamber 10 and to insure that new sample fluid effectively dominates any old fluid existing in the system. However, because of the exponential dilution property of the mixing chamber 10, this procedure in general requires a rather large infusion of concentrated fluid into the system.

Unfortunately, there are disadvantages with the injection of large amounts of concentrated fluid sample. First, the presence throughout the system of a large amount of concentrated fluid sample can exacerbate the normal problem of contamination of the optical surfaces of the flow-through scattering cell as well as surfaces elsewhere in the system. There is, of course, always some problem of contamination but it would be desirable not to increase this problem. Therefore, it is advantageous to minimize the exposure of the entire fluidic system to highly concentrated fluid samples to avoid having to frequently clean or otherwise maintain the system.

A second problem is that the total elapsed time needed to flush new fluid sample through the system and then obtain the desired large dilution factor suitable for a particular measurement or application may be prohibitively long, especially if there is a requirement of a short sampling/measurement cycle time. It can, therefore, be seen that it would be preferable to provide for another way in which to eliminate the problem of the dead sample volume.

The system of FIG. 5 provides for a method of avoiding this problem through the use of a more flexible fluidic system which precedes the input to the mixing chamber 10. As a specific example, the system of FIG. 5 includes the additional two-way valve 210 positioned in an outlet tubing 212 and with a pump 214 controlling the outflow of fluid through the line 212 to a drain 216. The two-way valve 210 would be controlled by the valve control 220 which in turn is controlled by the computer 218. In a typical operation, the old stagnant fluid sample from the dead volume in the tubing 14 is flushed out through the line 212 before the introduction of new fluid sample and fresh diluent into the mixing chamber. This can be accomplished using the following method.

The fluid pump 110 is not energized. The three-way valve 204 and the two-way valve 210 are both energized. Therefore, the normally-closed portion 206 of the three-way valve 204 is opened, thereby permitting a flow of sample material 200 into the system, and the normally-opened portion 208 of the three-way valve 204 is closed, so that the diluent 104 is not connected to the system. The normally-closed valve 210 is opened and the pump 214 is energized. The pump 214, therefore, pulls sample material 200 directly through the valve 210 to the drain 216.

When the flow of the concentrated sample material 200 has been established for a sufficient period of time to insure that the old stagnant sample has been completely displaced by new fresh sample, then both valves 204 and 210 are de-energized as well as the pump 214. The pump 110 is then energized, which has the effect of injecting a small quantity of fresh concentrated sample into the mixing chamber 10. This fresh sample would be that contained within the three-way valve and above the valve 210 and the associated tubing. The fresh sample is followed immediately by a continuous flow of diluent 104 from the diluent tank 106.

If additional concentrated sample material is necessary, then the valve 204 may be energized for a short period of time thereby injecting an additional quantity of fresh sample material into the mixing chamber 10 before the flow of diluent. In either event, a continuous dilution of the concentrated fluid sample then follows with the scattering intensity monitored at the flow-through cell 114 to achieve an appropriate scattering level and sample dilution. When the appropriate scattering level and sample dilution is reached, then the pump 110 is de-energized and the particle sizing measurement initiated in the measuring system using standard techniques.

It is to be appreciated that in some applications, the concentrated fluid sample 200 may be pressurized with respect to the prevailing system pressure. This could occur if the storage tank 202 is pressurized, or if the fluid sample is actually being supplied directly from a pressurized process stream. If the fluid sample is pressurized, then the pump 214 could be eliminated because the positive pressure would be sufficient to flush fluid sample through the drain line 216 once the valves 204 and 210 are energized. However, with such a pressurized fluid sample, it may be desirable to add another two-way valve before the entrance 12 to the mixing chamber 10. This would insure that there would be no partial injection of old fluid sample during the step of flushing. A specific example of a pressurized on-line system is the particle sizing of latex or other synthetic polymer emulsions directly from the pressurized reaction vessels in which these particles are made by emulsion polymerization.

The system of FIG. 5 offers additional flexibility because of the more complicated fluidic system compared with the system of FIG. 3. For example, if the starting fluid sample 200 is highly concentrated relative to the final desired concentration, it may be desirable to perform a predilution of the fluid sample using the same principle of continuous exponential dilution. This predilution occurs before injection into the main mixing chamber 10. In this embodiment, the tubing which interconnects the valves 204 and 210 and also the input port 12 of the mixing chamber 10 constitutes a miniture preliminary mixing chamber. After fresh concentrated fluid sample has been introduced into this tubing forming the miniture preliminary mixing chamber, then valve 204 can be de-energized but with valve 210 energized and pump 214 on. At this time fresh diluent 104 will be drawn by the pump 214 into the input tubing thereby diluting this concentrated sample contained within the small mixing chamber. Valve 210 and pump 214 can be energized for a fixed interval of time to achieve a predilution of the fluid sample prior to its injection into the main mixing chamber. This is accomplished by de-energizing the valve 210 and pump 12 and energizing the main flow pump 110 so that the now prediluted sample in the small mixing chamber is pulled into the main mixing chamber 10.

The embodiments of the present invention and specifically the use of dynamic light scattering shown in FIGS. 3 and 5 illustrate a specific example for the advantages of the present invention. In particular, the apparatus and method of the present invention is ideally suited to any measurement technique or processing procedure which requires as input a fluid sample whose solute concentration lies within a range which depends on the characteristics of the starting sample and, therefore, is not easily presetable using a conventional dilution method.

It should be appreciated that the specific embodiments of the present invention have been described using a specific component defined as a mixing chamber so as to achieve the exponential dilution of a starting sample. The use of such a mixing of the sample with a diluent is, of course, a general requirement of the present invention. However, this general requirement may be satisfied using structures other than a specific mixing chamber. In some applications, an actual tank or chamber or some other physically defined volumetric structure distinguished from the connecting tubing will be used to implement a particular embodiment of the invention. It should be appreciated, however, that the mixing chamber need not exist as a actual separate component of the example, since the interconnecting tubing itself may serve as a mixing chamber for the invention.

In particular, depending upon the flow velocity of the fluid sample and diluent and the size of the tubing used to connect the input sampling/injection system, with the downstream measuring or processing device, then the connecting tubing itself may serve as an appropriate mixing chamber. This may occur when the flow of diluent within the tubing is sufficiently fast and non-uniform to effect mixing and subsequent dilution of the injected fluid sample within the tubing so as to eliminate the need for a separate mixing chamber. The principles of the invention would work in such an environment even without a separate chamber.

In each of the representative dilution systems described above in connection with FIGS. 3 and 5, a 3-way valve has been used to direct the flow of either concentrated starting sample or diluent into the mixing chamber for the purpose of obtaining a continuous, variable dilution of the former. That is, concentrated sample alone is directed to the mixing chamber, followed by diluent alone. However, it should be evident that other injection schemes are possible and effective. For example, it may be desirable to inject a quantity of starting sample fluid into a stream of diluent which is already flowing into the mixing chamber. In this case, both the concentrated sample and fresh diluent can be made to enter the mixing chamber at the same time, rather than in the serial fashion described earlier. This operation can be achieved, for example, using a single 2-way valve, which connects the source of concentrated starting fluid to the tubing containing the diluent flowing into the input of the mixing chamber. The fluid which enters the latter would contain both concentrated sample and diluent at the outset of the dilution process, followed by diluent alone.

It should also be appreciated that with the QELS-based particle size measurement shown in the embodiments of FIGS. 3 and 5, the actual measurement occurs with the fluid sample statically contained within the measurement cell (i.e. no net fluid flow). However, there are certain measurement or process applications which for optimal performance require that the fluid sample continue to flow through some appropriate measurement component after the appropriate concentration is achieved For these cases, the present invention can still be used and even be enhanced by operating the system like a two-stage device. In equation 1, defined above, it can be seen that the exponential decay time constant of the dilutor ideally equals V/F, where V, is the volume of the mixing chamber and F the rate of flow of diluent into the chamber. While the volume is nominally fixed, the flow is in principle continuously variable. Therefore, the time constant for a decrease in solute concentration downstream of the mixing chamber can be varied over a substantial range by manipulation of the flow rate, F. As an example, the flow rate can be easily changed by using a variable speed pump.

As a specific example, a relatively high flow rate can be used at the onset of the dilution process to thereby achieve a short time constant. The solute concentration at the output of the mixing chamber will then fall relatively quickly in time. When an appropriate sample solute concentration is reached, as determined by a sample monitor device located downstream of the mixing chamber output, the flow pump may be automatically switched to a low speed thereby yielding a slower diluent flow rate $F'$ and a corresponding longer time constant $\tau'$. The monitoring device may, for example, be monitoring optical turbidity, electrical conductivity, light scattering intensity, etc.

At this point in the process, diluted fluid sample continues to flow through the measurement cell or process equipment, but at the lower flow rate $F'$. The solute concentration does continue to decrease in time, but at this slower rate. The new flow rate $F'$ can be made small enough to make $\tau'$ long enough so that the concentration $C(t)$ decreases only very slowly with time to permit the measurement or other process to be completed. If a higher absolute flow rate is required, then a larger mixing chamber volume would be incorporated into this system designed to permit both the initial and final flow rates to be scaled up appropriatly. The only difference with this change would be a decrease in the peak solute concentration which exits the mixing chamber, S/V, where S is the amount of injected sample.

In order to demonstrate the use of such a two-stage exponential dilution system, the following two examples are given. The first example involved is the measurement of particle size using the physical technique of Fraunhofer diffraction, or forward scattering applicable to larger particle diameters in the approximate range of 1-200 micrometers. In this type of measurement system, particles are dispersed either in a gas or liquid and are illuminated by a coherent laser beam of light. The individual particles diffract or scatter the incident light beam over a range of angles with most of the intensity occuring in the near-forward direction. An approximate particle size distribution is obtained by mathematical analysis of the angular dependence of the scattered intensity. Flowing the diluted particle suspension through the scattering cell effectively averages the scattered intensity patterns produced by a large number of particles. This improves the overall statistics and signal/noise ratio of the measurement. Dilution of the starting concentrated sample fluid is typically required for the Fraunhofer diffraction-based measurement. If there is too large a particulate concentration in the flow through cell, this causes multiple scattering and results in a distorted forward angle intensity pattern and an inaccurate computed particle sized distribution. If there is too small a concentration, this produces insufficient total light scattering or diffraction and results in a poor detector signal/noise ratio and a poorly defined size distribution and with prohibitively long data acquisition times.

The embodiments of the invention shown in FIGS. 3 and 5 may be easily adapted to a Fraunhofer-based measurement by using an appropriately design flow through scattering cell and associated optics and other instumentation. If the sample under measurement is a dry powder/gas mixture, then it may also be desirable to push the flow through the mixing chamber as opposed to pulling the flow, as shown in FIGS. 3 and 5. This is easily accomplished by moving the pump 110 to the input tubing 16 so that the diluent 104 will be pushed into the mixing chamber and carry with it the concentrated sample stored in the tubing in front of to the mixing chamber.

In such a Fraunhofer-based particle sizing system, it is also necessary to monitor the particulate concentration or some quantity which is representative of the concentration. This monitoring should occur either at, or in the vicinity of, the flow-through scattering cell. As an example, the monitoring may be a measurement of the total forward light scattering intensity which represents the optical turbitity of the fluid sample within the cell. Another example would be monitoring the scattered intensity at a large angle such as 90° or near 180°. Also the optical turbidity may be directly monitored just before or after the scattering cell. This monitoring would be used to control the other components of the automatic dilution system of the present system to provide for the two stages as described above.

Another example of a two-stage dilution system for a flow-through system is the measurement of particle size or molecular weight distribution using a sensor which is designed to respond to individual particles flowing in a fluid. This fluid may of course either be a gas, or a liquid. Typical sensors that may be used for this purpose include partial light obscuration or blockage within a small illuminated flow channel and light scattering intensity integrated over a large range of forward angles. In both cases, the sensor is designed to yield a signal whose amplitude increases monotonically with the mean diameter of the particle residing in the active area of the sensor for certain specified size ranges.

For both types of flow through sensors, the particle suspension must be diluted to a sufficient extent that, with high probability, there is at most only one particle at a time located within the sensitive measuring volume. It can be seen that too concentrated a sample causes frequent coincidences and associated false signals. Alternatively, too dilute a sample results in prohibitively long measurement times as well as excessive sensitivity to background contaminant particles which normally exist at low concentrations in typical gaseous and liquid diluents.

In this type of system, it would be inappropriate to establish a fixed dilution factor because typically the starting sample possesses an unknown number concentration of particles. Therefore, this type of system is ideal for the present invention, since the light obscuration or scattering sensing cell can be fed with the output of the exponential dilution mixing chamber and the pulse rate output of the sensor caused by the arrival of individual particles can be monitored. For a given flow rate, F, there is a maximum pulse rate beyond which there is a risk of obtaining an unacceptable percentage of particle coincidences which lead to a distorted particle size distribution.

Therefore, the dilution apparatus can be initially run at a relatively high flow rate, F, so as to quickly dilute the sample down to an acceptable sensor pulse rate. At this time, the processing of the individual pulses, such as a pulse height analysis, can be commenced so as to obtain the particle size distribution. To improve the performance of the signal processor, the flow pump can be slowed down to decrease the flow rate to F' which in turn decreases the pulse rate due to the arrival in the sensor of the new particles. The entire dilution/measurement cycle can be repeated any number of times so as to improve the statistics in the final particle size distribution. In this, as in any of the other embodiments, specific choices may be made of the mixing chamber volume, amount of injected sample and high/low flow rate so as to maximize the efficiency and speed of the measurement.

It should be appreciated that both of the application examples described above, particle sizing by Fraunhofer diffraction and by light obscuration or scattering by single particles, may be performed with the normal (single-stage) dilution apparatus. It is not necessarily the case that an effective measurement would benefit from, or require the use of, a second, slower diluent flow rate F'. Rather, data collection and processing may commence when the appropriate sample concentration is achieved, and the diluent flow rate F kept unchanged, without the need for lowering the flow rate. The two-stage dilution process was described above only as a possible useful variation of the basic dilution system described at the beginning of the application.

If can be seen, therefore, that the automatic dilution system of the present invention provides for a number of significant advantages. In particular, the invention may operate with a single or a repeated injection of a measured or unmeasured sample and still provide for the proper dilution. This is because the dilution which is provided is variable and becomes more extensive in time. In one aspect of the invention, only a small part of the sample which enters the dilutor is used in a measurement, but it is also possible to use a flow-through technique so that a continuous sample can be used in the measurement with the sample at a proper diluted concentration.

The invention operates using a relatively simple mechanism without any complicated parts. The invention is, in particular, useful for applications wherein the size of the dilution required for a measurement is unknown at the onset of the measurement. The invention provides for the proper dilution over a large dynamic range and is, therefore, particularly useful where large dilution factors are needed. Most importantly the invention operates to provide for the proper dilution factor without requiring an accurate metering of either the injected sample or the diluent. Although the invention has been described with reference to particular embodiments and also with reference to described additional adaptations and modifications of those embodiments, it is to be appreciated that the invention is not to be limited to these specific embodiments or described adaptations and modifications but is only to be limited by the appended claims.

We claim:

1. An automatic dilution system for providing a variable dilution of an unknown sample material, including
   a mixing chamber having at least one input and output, sample material and diluent,
   means for providing a single injection of a quantity of the sample material into the input of the mixing chamber,
   means for providing a flow of the diluent into the input of the mixing chamber to mix with the sample material and to continuously dilute the concentration of the sample material within the mixing chamber and flowing out of the mixing chamber to provide a variable dilution,
   means coupled to the output of the mixing chamber and responsive to the diluted sample material for providing a measurement of a particular characteristic of the continuously variable diluted sample material, and
   means coupled to the means for providing a flow of the diluent into the mixing chamber for controlling the flow of diluent in accordance with an optimal measurement of the particular characteristic.

2. The automatic dilution system of claim 1 wherein the mixing chamber is formed as a separate component in the system.

3. The automatic dilution system of claim 1 wherein the mixing chamber has only one input for receiving the sample material and the diluent.

4. The automatic dilutuion system of claim 1 additionally including means for receiving the sample material and the diluent for producing a predilution of the concentration of the sample material.

5. The automatic dilution system of claim 4 wherein the predilution means includes a predilution mixing chamber having at least one output connected to the input of the mixing chamber.

6. The automatic dilution system of claim 5 wherein the predilution mixing chamber is at least partially formed by tubing connecting the sample material and the diluent to the mixing chamber.

7. The automatic dilution system of claim 5 wherein the predilution means includes means for continuously diluting the concentration of the sample material within the predilution mixing chamber for a particular period of time.

8. The automatic dilution system of claim 7 wherein the means for continuously diluting includes a valve means connected to the predilution mixing chamber to control an outflow from another output of the predilution mixing chamber for the particular period of time.

9. The automatic dilution system of claim 1 wherein the means for providing the single injection includes a valve means having open and closed positions for controlling the injection of sample material.

10. The automatic dilution system of claim 1 wherein the means for providing a flow includes a valve means having open and closed positions for controlling the flow of the diluent.

11. The automatic dilution system of claim 1 additionally including a three way valve having two inputs and one output and with the inputs coupled to the means for providing the single injection and the flow means and the output coupled to the mixing chamber to control the injection of the sample material and the flow of the diluent to the mixing chamber and with the three way valve having open and closed positions to provide either injection of sample or flow of diluent to the mixing chamber but not both at the same time.

12. The automatic dilution system of claim 11 additionally including an additional valve having an input and output and with the output coupled to the input of the mixing chamber and with the input coupled to the means for providing the single injection and with the additional valve having an open position to draw off old sample material remaining in the system from a previous injection and to provide fresh sample material for a new injection.

13. The automatic dilution system of claim 12 wherein the operation of the three way valve and the additional valve additionally provides for a predilution of the concentrated sample material.

14. The automatic dilution system of claim 1 additionally including means to draw off old sample material remaining in the system from a previous injection to provide fresh sample material for a new injection.

15. The automatic dilution system of claim 1 wherein the measurement means is a light scattering detection system.

16. The automatic dilution system of claim 1 wherein the measurement means produces an output signal in accordance with the measurement of the particular characteristic and with the controlling means responsive to the output signal for controlling the flow of diluent.

17. The automatic dilution system of claim 16 wherein the controlling means includes a computer responsive to the output signal and with the computer programmed to control the flow of diluent.

18. The automatic dilution system of claim 1 wherein the controlling means controls the flow of diluent to stop when the optimal measurement of the particular characteristic is reached and with any further measurements of the diluted sample material provided on the diluted sample material in a static state.

19. The automatic dilution system of claim 1 wherein an initial flow of diluent into the mixing chamber is at a first rate of flow and wherein the controlling means controls the flow of diluent at a second rate of flow lower than the first rate of flow when the optimal measurement of the particular characteristic is reached and with any further measurement of the diluted sample material provided on the diluted sample material at the controlled low rate of flow.

20. The automatic dilution system of claim 1 wherein the variation of the continuous dilution of the concentration of the sample material is an exponential decay.

21. The automatic dilution system of claim 1 wherein the means for providing a flow of diluent includes a pump.

22. The automatic dilution system of claim 21 wherein the pump is located after the measurement means to pull the diluent through the mixing chamber.

23. The automatic dilution system of claim 1 wherein the means for providing a single injection of a quantity of sample material includes a syringe.

24. A method of providing an automatic variable dilution of an unknown sample material in a system having a mixing chamber having at least one input and output, sample material and diluent including the following steps:
singly injecting a quantity of the sample material into the input of the mixing chamber,
providing a flow of the diluent into the input of the mixing chamber to mix with the sample material and to continuously dilute the concentration of the sample material within the mixing chamber and flowing out of the mixing chamber to provide a variable dilution,
providing a measurement of a particular characteristic of the continuously variable diluted sample material, and
controlling the flow of diluent in accordance with an optimal measurement of the particular characteristic.

25. The method of claim 24 additionally including the step of producing a predilution of the concentration of the sample material.

26. The method of claim 25 wherein the step of predilution includes providing a predilution mixing chamber having at least one output connected to the input of the mixing chamber.

27. The method of claim 26 wherein the step of predilution includes the further step of continuously diluting the concentration of the sample material within the predilution mixing chamber for a particular period of time.

28. The method of claim 27 wherein the step of continuously diluting includes controlling an outflow from another output of the predilution mixing chamber for the particular period of time.

29. The method of claim 24 wherein the step of singly injecting includes controlling the injection of a known quantity of sample material.

30. The method of claim 24 wherein the step of providing a flow includes controlling the flow of the diluent at a known rate.

31. The method of claim 24 wherein the steps of injecting sample or providing a flow of diluent provide either injection of sample or flow of diluent to the mixing chamber but not both at the same time.

32. The method of claim 24 additionally the step of including means to draw off old sample material remaining in the system from a previous injection to provide fresh sample material for a new injection.

33. The method of claim 24 wherein the step of providing a measurement is a measurement of light scattering intensity.

34. The method of claim 24 wherein the step of providing a measurement produces an output signal in accordance with the measurement of the particular characteristic and with the step of controlling the flow responsive to the output signal to control the flow of diluent.

35. The method of claim 34 wherein the step of controlling the flow includes providing a computer responsive to the output signal and with the computer programmed to control the flow of diluent.

36. The method of claim 24 wherein the step of controlling the flow controls the flow of diluent to stop when the optimal measurement of the particular characteristic is reached and with any further measurements of the diluted sample material provided on the diluted sample material in a static state.

37. The method of claim 24 wherein the step of providing the flow of diluent into the mixing chamber is at a first rate of flow and wherein the step of controlling the flow controls the flow of diluent at a second rate of flow lower than the first rate of flow when the optimal measurement of the particular characteristic is reached and with any further measurement of the diluted sample material provided on the diluted sample material at the controlled low rate of flow.

38. The method of claim 24 wherein the step of providing a flow of diluent produces the continuous dilution of the concentration of the sample material as an exponential decay.

39. The method of claim 24 wherein the step of providing a flow of diluent pulls the diluent through the mixing chamber.

* * * * *